United States Patent [19]

Ooisi et al.

[11] Patent Number: 5,753,916
[45] Date of Patent: May 19, 1998

[54] DETECTOR FOR INFRAFRED GAS ANALYZER

[75] Inventors: Mituru Ooisi; Masahiro Uno; Mitsumi Nagumo, all of Tokyo, Japan

[73] Assignee: Fuji Electric Co., Ltd., Kawasaki, Japan

[21] Appl. No.: 804,167

[22] Filed: Feb. 20, 1997

[30] Foreign Application Priority Data

Feb. 22, 1996 [JP] Japan .................................. 8-034141

[51] Int. Cl.$^6$ .................................................. G01N 21/36
[52] U.S. Cl. .................... 250/345; 250/339.03; 250/343
[58] Field of Search ................................. 250/343, 345, 250/346, 338.1, 339.03, 339.13, 341.6

[56] References Cited

U.S. PATENT DOCUMENTS

| 4,692,622 | 9/1987 | Taniguchi et al. ............... 250/345 X |
| 5,468,962 | 11/1995 | Ohishi et al. ............... 250/343 |

FOREIGN PATENT DOCUMENTS

46-16787   5/1971   Japan .
52-39314   10/1977  Japan .

*Primary Examiner*—David P. Porta
*Attorney, Agent, or Firm*—Kanesaka & Takeuchi

[57] ABSTRACT

A detector for an infrared gas analyzer is formed of first and second light receiving rooms filled with gas to be analyzed, a gas passage communicating between the first and second light receiving rooms, and a heat-sensitive resistance element disposed perpendicularly to the gas passage. The heat-sensitive resistance element includes at least one heat insulator having an opening at a center thereof, a pair of heat-wire elements disposed on the heat insulator to face against each other with a predetermined space therebetween, and a heating device. Each heat-wire element has a plurality of elongated elements disposed parallel to each other in the opening of the heat insulator, and connecting portions for connecting ends of the elongated elements for serially connecting the elongated elements. The heating device is formed on the heat insulator around the opening to equalize temperature in a space surrounded by the heat-wire elements in the opening. Accordingly, the analyzer can be operated stably.

7 Claims, 6 Drawing Sheets

DETECTOR FOR INFRARED GAS ANALYZER

BACKGROUND OF THE INVENTION AND RELATED ART STATEMENT

The invention relates to a detector for an infrared gas analyzer, and more particularly, relates to a detector for an infrared gas analyzer which utilizes inherent absorptions of infrared rays by various gases and measures an amount of absorbed energy to analyze a constituent of a sample gas for a predetermined amount.

Figure 7:
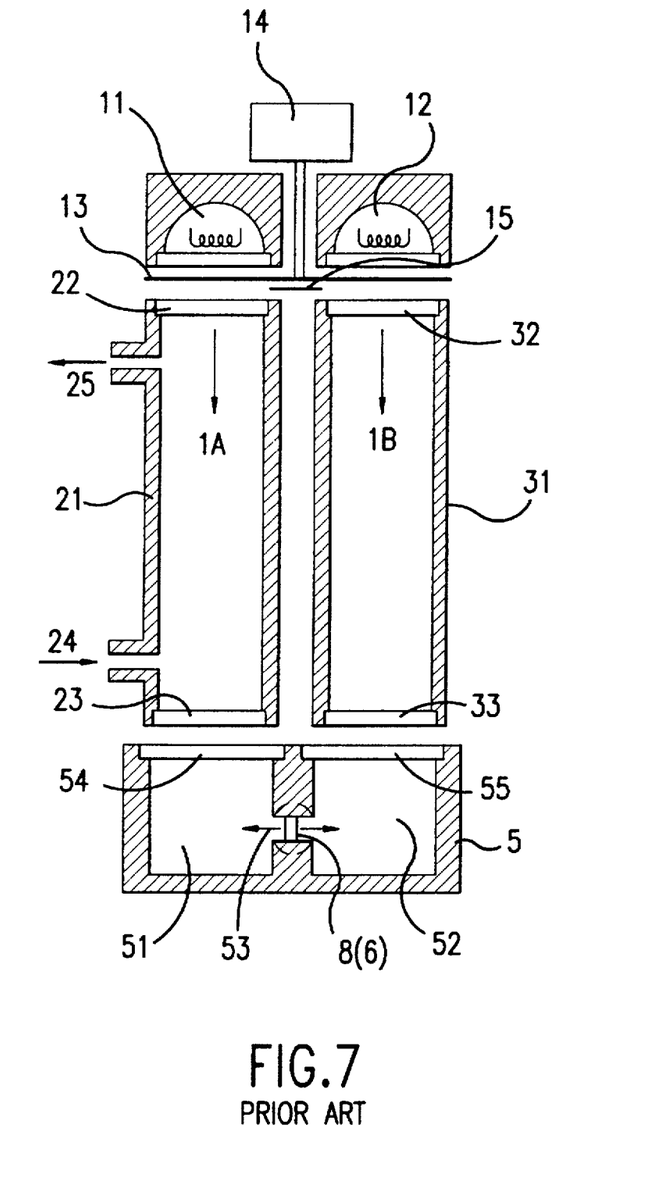
FIG. 7 is a schematic view for showing a detector and an infrared gas analyzer relating to the prior art and the present invention.

FIG. 7 shows a view for showing a general structure of an infrared gas analyzer and a detector therefor relative to the prior art and a present invention. In FIG. 7, the infrared gas analyzer includes an infrared source system for emitting a measuring ray 1A and a reference ray 1B. The infrared source system is formed of infrared ray sources 11, 12, a rotating chopper 13 for chopping infrared ray fluxes emitted from the infrared ray sources, a motor 14 for driving the rotating chopper 13, and a light adjustment trimmer 15 for adjusting an amount of the infrared ray flux.

The infrared gas analyzer also includes a measuring cell 21 disposed on a passageway of the measuring ray 1A and having introducing pipes 24, 25 for introducing and discharging a test sample gas including a gas to be analyzed which absorbs an infrared ray; and a reference cell 31 disposed on a passageway of the reference ray 1B wherein infrared ray is not substantially absorbed.

The infrared gas analyzer further includes a detector 5, which is formed of a first light receiving room 51 into which the measuring ray 1A passing through the test sample gas in the measuring cell 21 is emitted; a second light receiving room 52 into which the reference ray 1B passing through the reference cell 31 is emitted; a gas passage (hereinafter, referred as a communicating opening 53) communicating between the light receiving rooms 51, 52; and a heat sensitive resistance element 8 disposed perpendicularly to the communicating opening 53.

In the above structure, the infrared ray fluxes emitted from the infrared ray sources 11, 12 become interrupted lights in a specific cycle by the rotating chopper 13. One infrared ray flux is introduced as the measuring ray 1A into the measuring cell 21, and the other infrared ray flux is introduced as the reference ray 1B into the measuring cell 31. Unbalance of the amounts of the lights between the reference ray 1B introduced into the reference cell 31 and the measuring ray 1A introduced into the measuring cell 21 is adjusted by the light adjustment trimmer 15.

In the measuring cell 21, light transparent windows 22, 23 are provided, and a measuring gas including the gas to be analyzed is guided through the introducing pipes 24, 25 as indicated by arrows in the figure. The measuring ray 1A is infrared-absorbed in the measuring cell 21 according to a density of the gas to be analyzed in the measuring cell 21.

The reference cell 31 is also provided with light transparent windows 32, 33 and filled with a gas which does not absorb the infrared ray, such as a nitrogen gas. Thus, the reference ray 1B passes through the reference cell 31 without being affected by infrared absorption. The measuring ray 1A passing through the measuring cell 21 and the reference ray 1B passing through the reference cell 31 are introduced into the gas including type detector 5.

The detector 5 includes the first and second receiving rooms 51, 52, and the rooms 51, 52 are respectively provided with the light transparent windows 54, 55 and filled with the same kind of gas as the gas to be analyzed. The measuring ray 1A passes through the light transparent window 54 and enters into the first light receiving room 51, and the reference ray 1B passes through the light transparent window 55 and enters into the second light receiving room 52.

In the detector 5 shown in FIG. 7, at the communicating opening 53 for communicating between the first and second light receiving rooms 51, 52, based on the difference of the amounts of lights between the reference ray 1B and the measuring ray 1A infrared-absorbed in the measuring cell 21 according to the density of the gas to be analyzed, pressure fluctuation occurs in both the receiving rooms, so that a flow in proportion to a content of the analyzed gas in the test sample gas occurs. This flow is detected by a pair of the heat-sensitive resistance elements 8. Namely, the difference of the amount of light or ray between the measuring ray 1A and the reference ray 1B corresponds to the density of the analyzed gas in the test sample gas.

Figure 8A:
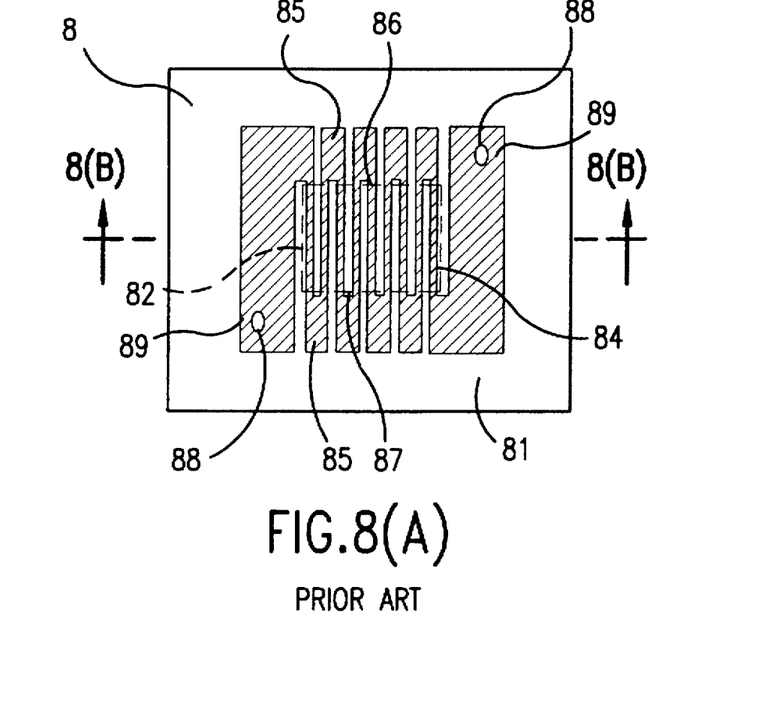
FIG. 8(A) shows a front view of the heat-sensitive resistance element.
Figure 8B:
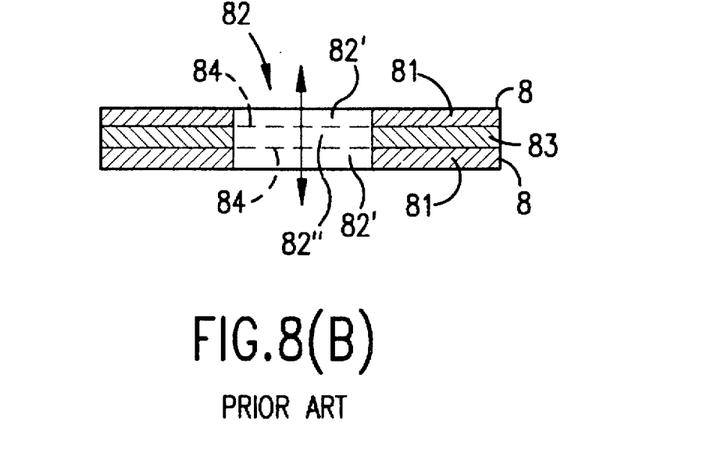
FIG. 8(B) is a sectional view taken along line 8(B)—8(B) in FIG. 8(A).

FIGS. 8(A) and 8(B) show the structure of a main part of the heat-sensitive resistance elements 8. FIG. 8(A) shows a front view of the heat-sensitive resistance element 8, and in FIG. 8(B), the heat-sensitive resistance elements 8 in a pair are disposed to face against each other with respect to a spacer 83 to constitute a sensing part of the detector 5.

In FIG. 8(A), the heat-sensitive resistance element 8 is formed of a heat insulator 81 having an opening part 82 in a center thereof; a heat-wire element 84 which is formed of either electrical conductive metal or electrical conductive ceramic, having a large temperature change for a resistance value, and includes a plurality of elongated band-like elements disposed in a traverse direction in the opening part 82; connecting portions 85 disposed on the heat insulator 81 for holding and securing the heat-wire element 84 and for electrically connecting the adjacent elongated elements; and terminal parts 89.

In the example shown in the figures, the heat insulator 81 is formed of an insulation substrate, such as a glass or ceramic, and at a center of the insulation substrate, the square opening part 82 as shown by a dotted line in FIG. 8(A) is disposed. Across the heat insulator 81 and the opening part 82, metal bands are disposed, and the heat-wire element 84 including the elongated elements is made from the metal bands, for example, by an etching-process. A gas flows in the spaces surrounded by the elongated elements of the heat-wire element 84. The elongated element 84 constitutes a conductor part of the heat-sensitive resistance element 8. Since the elongated elements of the heat-wire element 84 situated adjacent to each other are connected to each other by one of the connecting portions 85 on end surfaces 86, 87 of the opening part 82, the elongated elements of the heat-wire element 84 are altogether connected in a meandering state. Then, in the turning back points at the ends of the elongated elements in the meandering state, wide metal wires extend to constitute the terminal parts 89 as inlet and outlet for current, to which lead wires 88 are connected.

In the detector 5, in order to stably and efficiently detect a small gas flow in the communicating opening 53, the heat-sensitive resistance elements 8 are disposed to be adjacent to and to face against each other for a predetermined space therebetween. The sensing part of the aforementioned structure is shown in FIG. 8(B). In FIG. 8(B), the part shown by an arrow indicating both directions is a gas passage extending through the elongated elements of the heat-wire elements 84 for the heat-sensitive resistance elements 8 disposed inside the communicating opening 53. In the gas passage, a pair of the heat-wire elements 84 of the heat-sensitive resistance elements 8 are disposed to face against each other as shown by bold dotted lines in the figure. In the example shown in the figures, the heat-wire elements 84 of the heat-sensitive resistance elements 8 are disposed inwardly to face against each other, and attached together through a heat insulating material with a predetermined thickness, for example, a glass sheet 83 as a spacer.

The glass sheet 83 has an opening part 82" in a center part thereof, and the opening part 82" of the glass sheet 83 and opening parts 82' in the heat-sensitive resistance elements 8 are overlapped to form the common opening part 82. In the common opening part 82, a pair of the heat-wire elements 84 is disposed to have a space with the thickness of the glass sheet 83 therebetween and to be parallel to each other perpendicular to a gas flow direction.

The detector for the infrared gas analyzer according to the prior art has a following problem. Namely, in a pattern of the conductor part of the heat-sensitive resistance element as shown in FIG. 8(A), since heat heated by the heat-wire element through electrification is lowered by transferring to the connecting portions around the opening part and to the terminal parts, a temperature distribution occurs, in which the gas around the center of the opening part keeps high temperature, but the gas temperature around the end surfaces of the opening portion for the heat-wire elements is lowered nearly to a room temperature. As the detector for the infrared gas analyzer, the gas flow in the communicating opening is detected, but the temperature changes of both heat-wire elements by the gas flow are detected. Therefore, parts near the wall surfaces of the opening part which have low temperatures do not contribute as the detector to detect the gas flow in the communicating opening. Therefore, the temperature difference between the heat-wire elements is small, so that the output of the detector is merely proportional thereto.

In Japanese Patent Publication (KOKOKU) No. 52-39314, a detector for an infrared gas analyzer is basically formed of a first light receiving room in a measurement ray passage, a second light receiving room in a reference ray passage, a gas passage for communicating between the first and second light receiving rooms, and a heat-sensitive resistance element formed of heat-wire elements disposed in the gas passage to detect a gas flow in the gas passage. The heat-wire elements are formed in a meandering state in the gas passage, wherein outer portions of the heat-wire elements are also heated to contribute to measuring of the gas.

In Japanese Patent Publication (KOKOKU) No. 46-16787, a measurement device utilizes grids and a bridge circuit for detecting a small gas flow. The grids are heated by the bridge circuit. However, it is preferable to improve sensitivity.

In view of the foregoing, an object of the invention is to solve the aforementioned problem, and to provide the detector for the infrared gas analyzer which equalizes a temperature distribution and improves a detecting sensitivity without losing stability of the detector.

SUMMARY OF THE INVENTION

To achieve the aforementioned object, the present invention provides a detector used for an infrared gas analyzer, which comprises: a first light receiving room which is disposed in a measuring ray passage and into which the measuring ray passing through a sample test gas containing a gas to be analyzed absorbing an infrared ray is emitted; a second light receiving room which is disposed in a reference ray passage and into which a reference ray without being subjected to infrared ray absorption is emitted; a gas passage for communicating between the first and second light receiving rooms; and a heat-sensitive resistance element disposed in the gas passage perpendicular thereto.

Furthermore, in the detector of the invention, the first and second light receiving rooms are filled with the same kind of gas as the gas to be analyzed. The heat-sensitive resistance element is formed of a heat insulator having an opening part at a center thereof; heat-wire elements which face against and are spaced apart from each other with a predetermined distance, each being made of either electrical conductive metal or electrical conductive ceramic having a large temperature change for a resistance value and including a plurality of elongated band-like elements disposed in the opening part parallel to each other and serially connected together by connecting portions; and heating means disposed on the heat insulator around the opening part.

According to the aforementioned structure, a space temperature surrounded by both heat-wire elements in the opening part of the heat-sensitive resistance element can be equalized, and while the highest temperature inside the opening part is maintained within a certain range, with respect to the small gas flow, transfer of heat from a upstream side to a downstream side can be efficiently carried out. Consequently, the detecting sensitivity of the heat-wire element of the heat-sensitive resistance element regarding the small gas flow can be improved.

Also, the heat-sensitive resistance element can be provided with extensions of the elongated band-like elements of the heat-wire element which extend for a predetermined distance on the heat insulator; connecting portions for connecting adjacent band-like elements of the heat-wire element; and terminal parts.

In the above structure, the extensions and connecting portions also function as the heating means, and by electrifying the heat-wire elements, Joule heat is generated on the heat-wire element on the opening part and the connection portions on the heat insulator, so that transfer of heat from the heat-wire element in the opening part to the connecting portions on the heat insulator can be prevented. Therefore, the average temperature of the heat-wire element inside the opening part can be increased, and accordingly the detecting sensitivity can be improved.

Also, a pattern area of the terminal part can be minimized to enable a connection of the lead wires, and auxiliary heating elements can be disposed around the heat-wire element on the heat insulator.

According to the above structure, the heating means of the heating insulator can be provided around all four side areas of the opening part, to thereby provide an equal temperature distribution in which the average temperature inside the opening part is close to the predetermined highest temperature. Thus, the detecting sensitivity with respect to a small gas flow can be improved.

Also, the connecting portions can be made in a minimum dimension necessary to hold the heat-wire element on the opening part, and the auxiliary heat elements can be provided in a substantially entire area around the opening part.

According to the aforementioned structure, by providing the auxiliary heat elements in the substantially entire area around the opening part, the equal temperature distribution with the high average temperature can be achieved inside the opening part, and the detecting sensitivity with respect to the small gas flow can be improved. Also, the resistance element of the heat-wire element forming a detection bridge circuit can be formed of the resistance elements of the heat-wire element in the opening part contributing to detect the temperature change by the gas flow in the opening part. Consequently, the detecting sensitivity of the bridge circuit can be improved without losing the stability thereof due to a surrounding temperature change of the detector and so on.

BRIEF DESCRIPTION OF THE DRAWINGS

FIGS. 8(A) and 8(B) show a structure of a main part of a conventional heat-sensitive resistance element, wherein

DETAILED DESCRIPTION OF PREFERRED EMBODIMENTS

Figure 1:
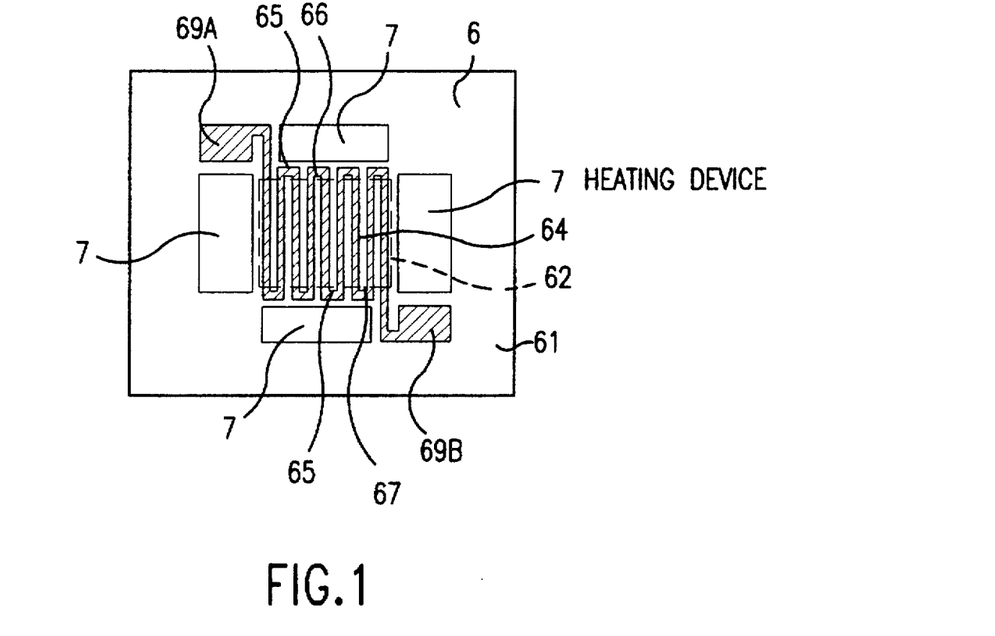
FIG. 1 is a view for showing a main structure of a heat-sensitive resistance element of a detector for an infrared gas analyzer according to the present invention.
Figure 2:
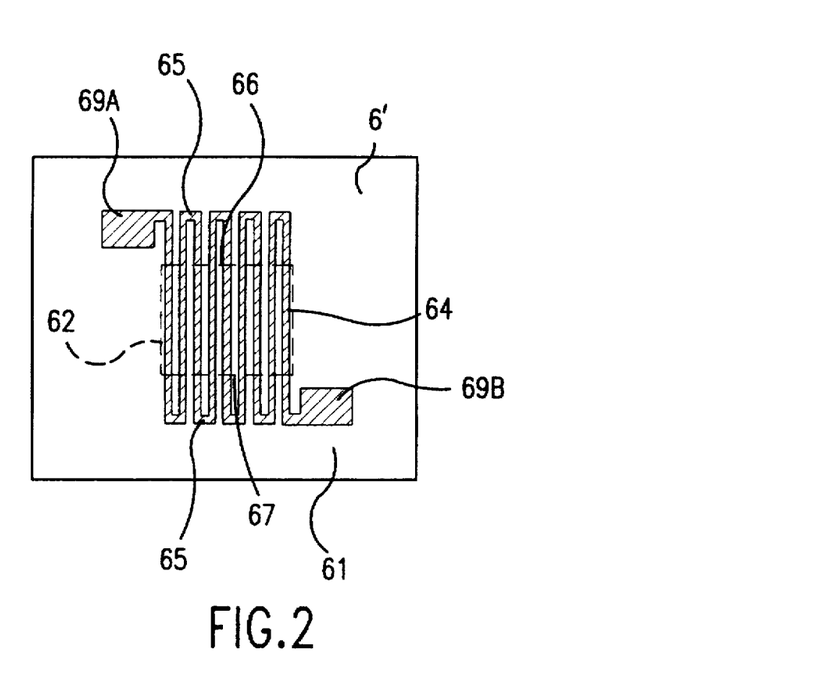
FIG. 2 is a view for showing a main structure of a heat-sensitive resistance element according to a first embodiment of the invention.
Figure 3:
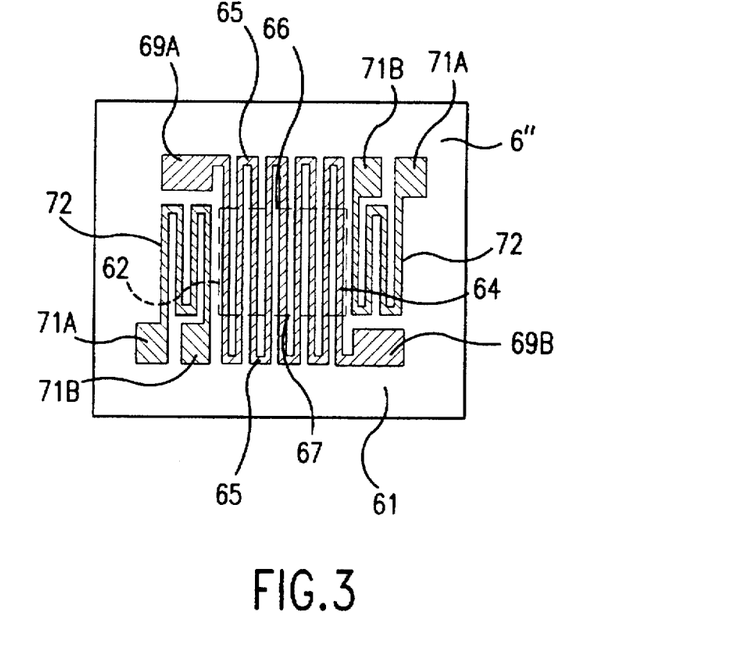
FIG. 3 is a view for showing a main structure of a heat-sensitive resistance element according to a second embodiment of the invention.
Figure 4:
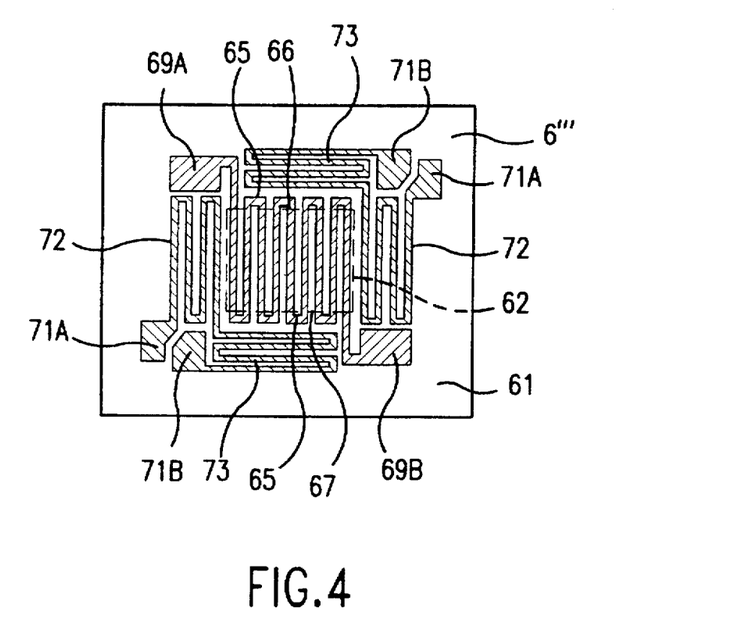
FIG. 4 is a view for showing a structure of a heat-sensitive resistance element according to a third embodiment of the invention.
Figure 5A:
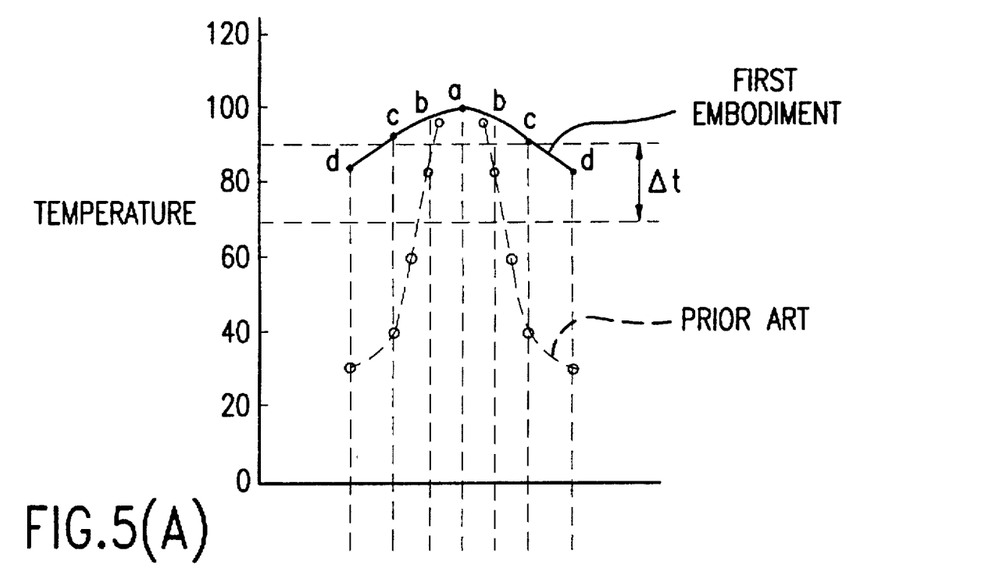
FIG. 5(A) is a characteristic graph showing a temperature distribution at an opening part.
Figure 6A:
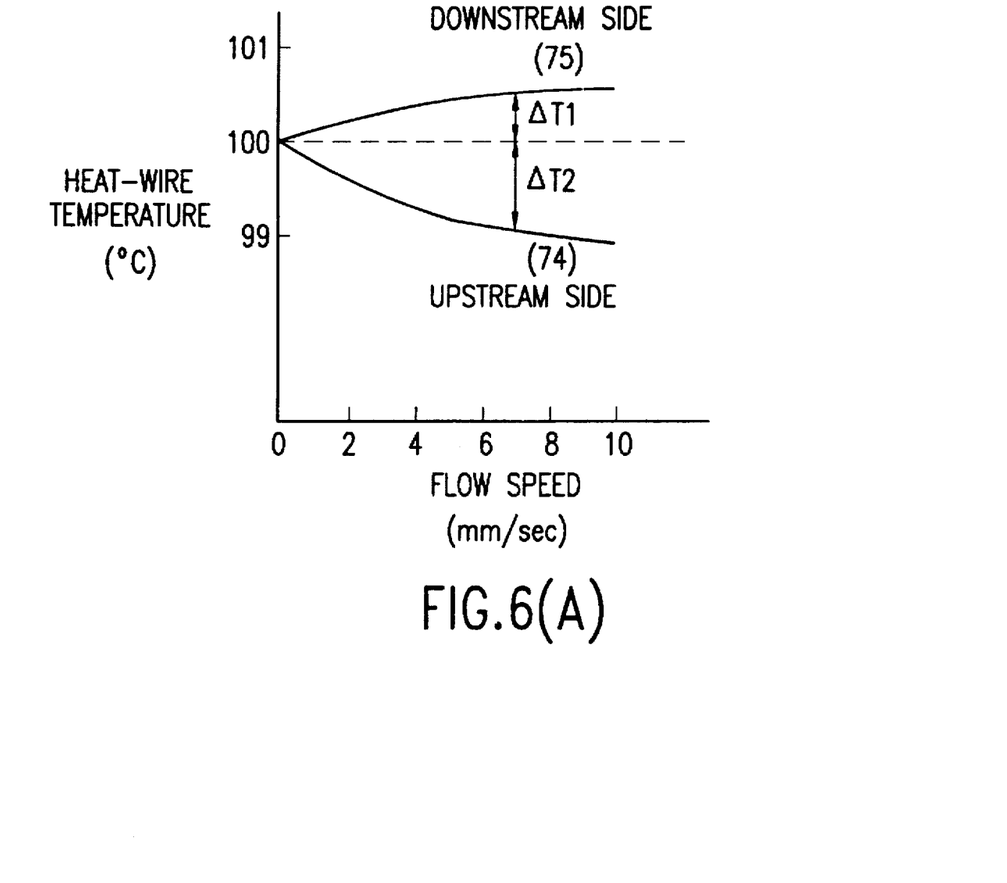
FIG. 6(A) is a characteristic graph showing a temperature of the heat-wire element according to the gas flow.

FIG. 1 is a view for showing a main part of a heat-sensitive resistance element of a detector for an infrared gas analyzer according to the present invention; FIGS. 2, 3 and 4 are views for showing main parts of the heat-sensitive resistance elements according to the embodiments of the invention; FIG. 5(A) is a characteristic graph showing a temperature distribution on an opening part; and FIG. 6(A) is a characteristic graph showing a temperature of the heat-wire element according to a gas flow speed.

An infrared gas analyzer of the invention is explained with reference to FIGS. 1 and 7. In FIG. 7, a detector 5 for an infrared gas analyzer is formed of a first light receiving room 51 which is disposed in a passageway of a measuring ray 1A and into which the measuring ray 1A passing through the test sample gas including the gas to be analyzed and absorbing an infrared ray is emitted; a second light receiving room 52 which is disposed in a passageway of a reference ray 1B and into which the reference ray 1B not subjected to the infrared absorption is emitted; a communicating opening 53 as a gas passage for communicating between the light receiving rooms 51, 52; and a pair of heat sensitive resistance elements 8 disposed perpendicularly to the passageway of the communicating opening 53 to face against each other with a predetermined space. The receiving rooms 51, 52 are filled with the same kind of a gas as the gas to be analyzed. In the invention, heat sensitive resistance elements 6 are used instead of the heat sensitive resistance elements 8 as shown in FIG. 7.

In FIG. 1, the heat-sensitive resistance element 6 is formed of a heat insulator 61 having an opening part 62 at a center thereof; a heat-wire element 64 which is made of either electrical conductive metal or electrical conductive ceramic having a large temperature change for a resistance value, and includes a plurality of elongated band-like elements disposed parallel to each other and connected in series at connecting portions 65; and heating devices 7 which are disposed on the heat insulator 61 around the opening part 62.

In the above structure, since a peripheral temperature of the heat insulator 61 is increased by the heating device, when the heat-wire element 64 is electrified, Joule heat of the heat-wire element 64 around the opening part 62 is prevented from escaping to the connecting portion 65 to thereby equalize a temperature in a space surrounded by the heat-wire elements at the opening part of the heat-sensitive element. Consequently, while maintaining the highest temperature inside the opening part within a predetermined range, with respect to a small gas flow, heat can be transferred efficiently from an upstream side to a downstream side thereof to improve the detecting sensitivity of the heat-wire elements against the small gas flow.

Next, a heat-sensitive resistance element 6' according to a first embodiment of the invention is explained with reference to FIG. 2. In FIG. 2, a heat-sensitive resistance element 6' is formed of a heat insulator 61 having an opening part 62 in a center thereof; a heat-wire element 64 which is formed of either electrical conductive metal or electrical conductive ceramic, having a large temperature change for a resistance value, and includes a plurality of elongated band-like elements disposed in a traverse direction in the opening part 62; a plurality of connecting portions 65 which is disposed on the heat insulator 61 for holding and securing the heat-wire element 64 and for electrically connecting the adjacent band-like elements of the heat-wire elements 64, and which has a width substantially the same as the width of the heat-wire element 64; and terminal parts 69A, 69B.

In the above structure, while the heat-wire elements are disposed in the opening part 82 in the prior art, in the present invention, the heat-wire elements crossing the opening part 62 extend in the longitudinal direction thereof for a predetermined distance on the heat insulator 61, so that the extended connecting portions 65 also function as the heating devices. When the heat-wire element 64 is electrified, Joule heat is generated at the heat-wire element 64 on the opening part 62 and at the connecting portions 65 on the heat insulator 61. As a result, heat transfer from the heat-wire element 64 in the opening part 62 to the connecting portions 65 on the heat insulator 61 can be prevented, and the average temperature of the heat-wire in the opening part 62 can be increased to thereby improve the detecting sensitivity. Therefore, the small gas flow in the communicating opening can be detected with high-sensitivity.

Figure 5B:
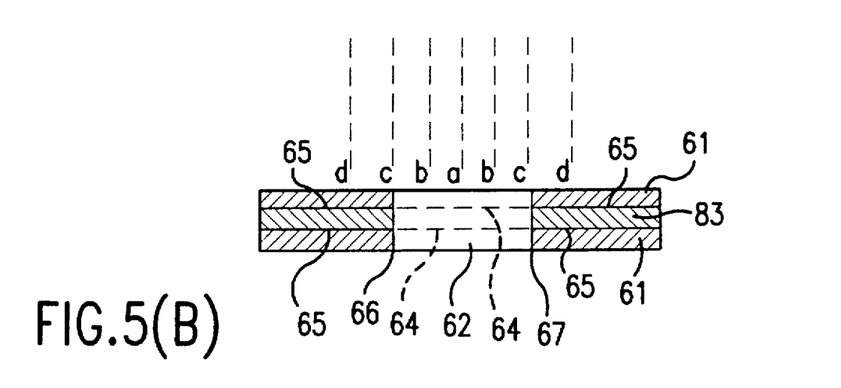
FIG. 5(B) is a side view of the heat-sensitive resistance element showing measuring points of FIG. 5(A)

FIG. 5(A) shows a temperature distribution characteristic according to the first embodiment of the invention. Firstly, a sensing part of the detector 5 is explained with reference to FIG. 5(B). In FIG. 5(B), the sensing part is constituted by a pair of the heat-sensitive elements 6 having the spacer 83 therebetween and facing against each other with a predetermined space. Here, the heat-sensitive resistance element 6 shown in FIG. 5(B) is a side view wherein the heat-sensitive resistance element 6 shown in FIG. 2 is rotated at 90 degrees. Namely, in the sensing part of the detector 5, the heat-wire elements 64 and the connecting portions 65 are respectively formed on the surfaces of the heat insulators 61, and are disposed inwardly to face against each other. The opening part 62 and the end surfaces 67, 68 of the spacer 83 are aligned to form the gas passage in a space between the respective heat-wire elements 64. Then, a central point of the opening part 62 is designated as a measuring point a, the end surfaces 66, 67 of the opening part are designated as measuring points c, intermediate points, each being located between the central point and the end surface, are designated as measuring points b, and points on the connecting portions 65 are designated as measuring points d.

Next, the temperature distribution characteristic is explained with reference to FIG. 5(A). In FIG. 5(A), the ordinate shows temperature, and the abscissa shows the aforementioned measuring points. In FIG. 5(A), measured data in the prior art are shown by tiny blank circles (o) and dotted lines connecting therebetween, and measured data in the first embodiment of the invention are shown by tiny blackened circles (●) and solid lines connecting therebetween. In both measured data, a temperature at the central point a of the opening part 62 is 100° C. According to the measured data, the average temperature of the heat-wire element 64 in the prior art is approximately 70° C., and in accordance with the structure of the invention, the average temperature of the heat-wire element 64 is improved to be about 90° C. Namely, when the invention is compared to the prior art, the average temperature of the heat-wire element 64 is increased as Δt≈20° C. to improve approximately 30 to 50% of the average temperature. Therefore, the sensitivity of the detector 5 can be improved by 1.3 to 1.5 times.

Figure 6B:
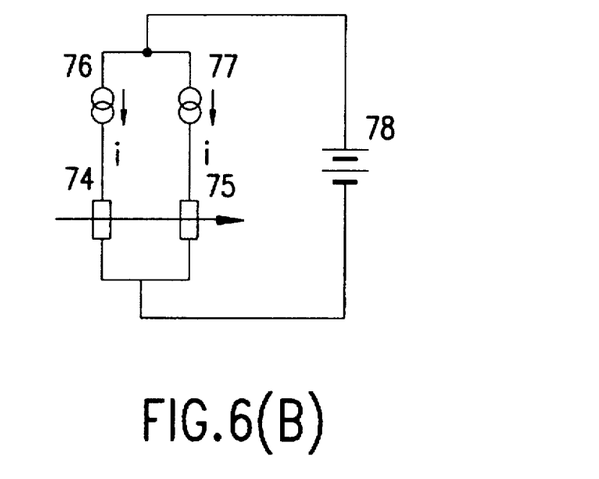
FIG. 6(B) is a diagram for showing constant-current sources and upstream and downstream side sensors.

FIG. 6(A) shows temperature changes of an upstream side sensor 74 and a downstream side sensor 75 (hereinafter, the heat-wire element 64 at the upstream side is referred to as the sensor 74, and the heat-wire element 64 at the downstream side is referred to as the sensor 75). In FIG. 6(B), constant-current sources 76, 77 supply currents i to the sensors 74, 75, and in a state of the temperature distribution as shown by the solid lines in FIG. 5(A), a gas is flown from the upstream side sensor 74 to the downstream side sensor 75. Temperature changes of the upstream and downstream side sensor 74, 75 at this state are, as shown in FIG. 6(A), described such that the heat of the upstream side sensor 74 is absorbed by the gas flow to lower the temperature thereof and to decrease the electric resistance. On the other hand, the downstream side sensor 75 is heated by the flow of the gas absorbing the heat from the upstream side sensor 74 and increasing the temperature thereof to thereby increase the electric resistance.

If an amount of the heat taken from the upstream side sensor 74 is all transferred to the downstream side sensor 75, FIG. 6(A) is supposed to show the symmetrical changes with the sensor temperature at 100° C. as a center. In reality, as shown in FIG. 6(A), a temperature change of the downstream side sensor 75 is smaller. To improve the detecting sensitivity of the detector 5, the sum of the temperature change ΔT2 of the upstream side sensor 74 and the temperature change ΔT1 of the downstream side sensor 75, i.e. ΔT1+ΔT2, should be increased. By increasing the average temperature of the heat-wire element 64, the difference between the temperature changes of the sensors 74, 75 (ΔT1+ΔT2) can be increased.

FIG. 3 is a view of a heat-sensitive resistance element 6" according to a second embodiment of the invention. In this structure, the structure of the heat-wire element 64 as shown in FIG. 2, or the terminal parts 89 in the prior art as shown in FIG. 8, are minimized to have a space around the heat-wire element 84, and as shown in FIG. 3, auxiliary heat elements 72 are provided on the substrate of the same heat insulator 61.

In the above structure, by electrifying and heating the auxiliary heat elements 72, it is prevented that the temperature of the heat-wire element 64 is decreased due to radiation of a heat from the heat-wire element 64 to the substrate of the heat insulator 61 or to the atmosphere. Then, comparing to the structure of the prior art which does not have the auxiliary heat elements 72, this structure can provide a temperature distribution around the opening part 62 with equal and high average temperature. Thus, the detector 5 with sensitivity higher than that of the structure in the first embodiment can be obtained.

FIG. 4 is a view of the heat-sensitive resistance element 6"' according to a third embodiment of the invention. This structure is constituted such that the connecting portions 65 formed on the heat insulator 61 as shown in FIG. 3 are minimized necessary to hold the heat-wire element 64 in the opening part 62, and the auxiliary heat elements 72, 73 are provided in the substantially entire area around the opening part.

In the above structure, by electrifying and heating the auxiliary heat elements 72, 73, temperature decrease of the heat-wire element 64 caused by radiating a heat from the heat-wire element 64 to the substrate of the heat insulator 61 or to the atmosphere can be prevented. Therefore, as described in the second embodiment, an equal temperature distribution with a high average temperature in the opening part 62 can be achieved, and the detector 5 with the high-sensitivity can be obtained.

Also, in the structure of the third embodiment, since the connecting portions 65 which do not directly contribute to detect the gas flow are constructed in the minimum dimension necessary to hold and secure the heat-wire element 64 on the opening part 62, the resistance value of the connecting portions 65 can be minimized. Thus, detecting resistances 74, 75 of a bridge circuit shown in FIG. 6(B) can be minimized as required.

To improve the detecting sensitivity, the detecting resistances 74, 75 are formed of conductive metal or electrical conductive ceramic in which resistance value is changed greatly by the temperature change. Therefore, deviation in the resistance value of the detecting resistances 74, 75 as described above is affected by the change of a surrounding temperature, for example, zero-point change, so that it might cause a problem in a zero-point stability as the detector 5. In the structure of the third embodiment, since the resistance value of the detecting resistances 74, 75 can be minimized as required, the detector with the high sensitivity can be constructed without losing the stability of the detector.

In FIG. 5(B), it has been explained that the heat-sensitive resistance element 6 is formed of two heat insulators 61, each having the heat-wire element 64 and the connecting portions 65 formed on one surface thereof, between which the spacer 83 having the heat insulating characteristic is interposed. The respective surfaces with the heat-wire elements 64 and the connecting portions 65 face the spacer 83. However, it is possible to form the heat-sensitive resistance element 6 such that at a position of the spacer 83, a heat insulator 61 is disposed; the heat-wire elements 64 and the connecting portions 65 are formed on both surfaces of the heat insulator 61; and outside the connecting portions 65, i.e., a position where the heat insulator 61 is located in the figure, protecting members formed of heat insulating materials, such as a glass are formed.

As described above, according to the structures of the invention, the heat-sensitive resistance element is provided with heating devices formed on the heat insulator around the opening part, and by heating of the heating device, Joule heat of the heat-wire element can be prevented from escaping to the heat insulator. Therefore, the space temperature surrounded by both of the heat-wire elements disposed inside the opening part of the heat-resistance element can be equalized, and the average temperature can be increased. As a result, since the lower temperature part contributing little to measuring and detecting in the prior art can be eliminated, the heat-wire element inside the opening part can contribute equally to detect a temperature to thereby improve the sensitivity of the detector. Also, the resistance value of the connecting part can be minimized, and by providing the heating devices around the opening part, the present invention can provide the detector for the infrared gas analyzer in which the detecting sensitivity is improved without losing the stability of the detector.

While the invention has been explained with reference to the specific embodiments of the invention, the explanation is illustrative and the invention is limited only by the appended claims.

What is claimed is:

1. A detector for an infrared gas analyzer, comprising:
   a first light receiving room filled with a gas to be analyzed;
   a second light receiving room situated adjacent to the first light receiving room and filled with the gas to be analyzed;
   a gas passage communicating between the first light receiving room and the second light receiving room; and
   a heat-sensitive resistance element disposed perpendicularly to the gas passage and including at least one heat insulator having an opening at a center thereof; a pair of heat-wire elements disposed on the at least one heat insulator to face against each other with a predetermined space therebetween, each heat-wire element having a plurality of elongated elements disposed parallel to each other in the opening of the heat insulator and connecting portions for connecting ends of the elongated elements for serially connecting the elongated elements; and heating means formed on the heat insulator around the opening to equalize temperature in a space surrounded by the heat-wire elements in the opening.

2. A detector for an infrared gas analyzer according to claim 1, wherein each of said heat-wire elements is formed of one of an electrical conductive metal and an electrical conductive ceramic, which has a large temperature change for a resistance value.

3. A detector for an infrared gas analyzer according to claim 2, wherein each of said elongated elements of the heat-wire element includes extensions with predetermined lengths situated on the heat insulator and a width as in each of the connecting portions, said elongated elements being connected by the connecting portions at the extensions, said heating means being formed of the extensions and the connecting portions.

4. A detector for an infrared gas analyzer according to claim 3, wherein said heat-sensitive resistance element further includes terminal parts with pattern areas on the heat insulator which are minimum necessary to connect lead wires therein, and at least one auxiliary heating element formed separately from the heat-wire elements and disposed around the heat-wire elements on the heat insulator.

5. A detector for an infrared gas analyzer according to claim 2, wherein each connecting portion has a minimum dimension necessary to connect the elongated elements on the insulator, said heat-sensitive resistance element further including a plurality of auxiliary heating elements disposed on the heating insulator to surround a circumference of the opening.

6. A detector for an infrared gas analyzer according to claim 1, wherein said first light receiving room is disposed in a measuring ray passage and receives a measuring ray passed through a test sample gas containing the gas to be analyzed, said gas to be analyzed absorbing an infrared ray, and said second light receiving room is disposed in a reference ray passage and receives a reference ray in which the infrared ray was not absorbed.

7. A detector for an infrared gas analyzer according to claim 1, wherein said heat-sensitive resistance element includes two heat insulators, and a spacer, each of said heat-wire elements being disposed on one side of each heat insulator and arranged such that the heat-wire elements on the heat insulators face against each other through the spacer.

* * * * *

UNITED STATES PATENT AND TRADEMARK OFFICE
CERTIFICATE OF CORRECTION

PATENT NO. : 5,753,916
DATED : May 19, 1998
INVENTOR(S) : Mituru Ooisi, Masahiro Uno, Mitsumi Nagumo It is certified that error appears in the above-indentified patent and that said Letters Patent is hereby corrected as shown below:

Title page, item [54] Title of the Invention, change "INFRAFRED" to --INFRARED--;

In column 1, line 1, change "INFRAFRED" to --INFRARED--;

In column 4, line 59, change "on" to --in--;

In column 6, line 49, change "on the opening" to --in the opening--;
line 63, before "element" add --resistance--;
line 67, change "6" to --6'--;

In column 7, line 5, change "67, 68" to --66, 67--;
line 43, change "sensor" to --sensors--;

In column 8, line 1, change "Fig. 8" to --Fig. 8(A)--;
line 9, change "comparing" to --compared--; and
line 10, change "to" to --with--.

Signed and Sealed this

Seventeenth Day of November, 1998

Attest:

BRUCE LEHMAN

*Attesting Officer*    *Commissioner of Patents and Trademarks*